United States Patent
Moore et al.

(10) Patent No.: US 6,649,719 B2
(45) Date of Patent: Nov. 18, 2003

(54) DEGRADABLE, AMORPHOUS, FLUOROCHEMICAL ACRYLATE POLYMERS

(75) Inventors: George G. I. Moore, Afton, MN (US); Michael A. Yandrasits, Hastings, MN (US); Jay F. Schulz, Inver Grove Heights, MN (US); Richard M. Flynn, Mahtomedi, MN (US)

(73) Assignee: 3M Innovative Properties Company, St. Paul, MN (US)

(*) Notice: Subject to any disclaimer, the term of this patent is extended or adjusted under 35 U.S.C. 154(b) by 100 days.

(21) Appl. No.: 09/931,215

(22) Filed: Aug. 16, 2001

(65) Prior Publication Data

US 2002/0042470 A1 Apr. 11, 2002

Related U.S. Application Data

(60) Provisional application No. 60/226,235, filed on Aug. 18, 2000.

(51) Int. Cl.$^7$ ................................................. C08F 14/18
(52) U.S. Cl. ....................... 526/245; 524/544; 560/223; 564/209
(58) Field of Search ......................... 526/245; 524/544; 560/223; 564/209

(56) References Cited

U.S. PATENT DOCUMENTS

| | | |
|---|---|---|
| 2,666,797 A | 1/1954 | Husted et al. |
| 2,803,615 A | 8/1957 | Ahlbrecht et al. |
| 2,841,573 A | 7/1958 | Ahlbrecht et al. |
| 3,341,497 A | 9/1967 | Sherman et al. |
| 3,398,182 A | 8/1968 | Guenthner et al. |
| 3,462,296 A | 8/1969 | Raynolds et al. |
| 3,896,251 A | 7/1975 | Landucci |
| 3,923,815 A | 12/1975 | Dettre et al. |
| 4,001,305 A | 1/1977 | Dear et al. |
| 4,029,585 A | 6/1977 | Dettre et al. |
| 4,264,484 A | 4/1981 | Patel |
| 4,792,354 A | 12/1988 | Matsuo et al. |
| 4,849,291 A | 7/1989 | Yacobucci et al. |
| 5,223,593 A | 6/1993 | McAllister et al. |
| 5,274,159 A | 12/1993 | Pellerite et al. |
| 5,410,073 A | 4/1995 | Kirchner |
| 5,578,278 A | 11/1996 | Fall et al. |
| 5,688,884 A | 11/1997 | Baker et al. |
| 5,772,817 A | 6/1998 | Yen et al. |
| 6,005,137 A | 12/1999 | Moore et al. |
| 6,037,429 A | 3/2000 | Linert et al. |
| 6,238,798 B1 | 5/2001 | Kang et al. |

FOREIGN PATENT DOCUMENTS

| | | |
|---|---|---|
| EP | 0 889 092 | 1/1999 |
| FR | 2 592 055 | 6/1987 |
| JP | 04025569 A2 * | 1/1992 |
| WO | WO 00/50517 | 8/2000 |
| WO | WO 01/05468 A2 | 1/2001 |
| WO | WO 01/30873 A1 | 5/2001 |

OTHER PUBLICATIONS

Abe, T. et al., "Electrochemical Fluorination (Simons Process)as a Route to Perfluorinated Organic Compounds of Industrial Interest", *Preparation, Properties, and Industrial Applications of Organofluorine Compounds*, p. 26 (1982).
Bernett, M. et al., "Wetting of Low–Energy Solids by Aqueous Solutions of Highly Fluorinated Acids and Salts", *The Journal of Physical Chemistry*, vol. 63, No. 11, pp. 1911–1916 (Nov. 1959).
Brace, N., "Long Chain Alkanoic and Alkenoic Acids with Perfluoroalkyl Terminal Segments", *The Journal of Organic Chemistry*, vol. 27, pp. 4491–4498 (Dec. 1962).
Dobrowolski, J., "Antireflection Coatings", *Handbook of Optics*, vol. 1, pp. 42.19–42.34 (1995).
Hendricks, J., "Industrial Fluoro–Chemicals", *Industrial and Engineering Chemistry*, vol. 45, No. 1, pp. 99–105 (Jan. 1953).
Kirk–Othmer, Waterproofing and Water/Oil Repellency, *Encyclopedia of Chemical Technology*, Third Edition, vol. 24, pp. 448–462 (1984).
*Organofluorine Chemicals and their Industrial Applications*, pp. 56–61 (1979).
Saloutina, L. et al., "Synthesis and Reactions of Oxygen–Containing Organofluorine Compounds", *Journal of Organic Chemistry of the USSR*, vol. 18, No. 4, Part 1, pp. 685–689 (Apr. 1982).
Tatlow, J., "Aspects of Organofluorine Chemistry", *Organofluorine Chemicals and their Industrial Applications*, pp. 19–43 (1979).
Zisman, W., "Relation of the Equilibrium Contact Angle to Liquid and Solid Constitution", *Contact Angle, Wettability, and Adhesion*, pp. 1–51 (1964).
CRC Handbook of Chemistry and Physics, 72$^{nd}$ Edition, 1991–1992, p. 102–90, Lide.
Polymer Handbook, 4$^{th}$ Edition, 1999. p. VI/578, Brandrup et al.

* cited by examiner

*Primary Examiner*—David W. Wu
*Assistant Examiner*—Satya B Sastri
(74) *Attorney, Agent, or Firm*—Robert H. Jordan

(57) ABSTRACT

Described is a compound having at least one acrylate monomer, said monomer including at least one pendant group of the structure —O—CH($R_f$)($R_f'$), wherein $R_f$ is a straight chain or branched perfluoroalkyl group with five or less carbon atoms, and $R_f'$ is a branched perfluoroalkyl group with three to five carbon atoms; and a method of reducing the surface tension of a liquid by adding a compound of the invention to the liquid. Also described is a composition that includes a compound of the invention in an aqueous solution or dispersion; a method of treating a substrate to render it oil- and/or water-repellent that includes treating a substrate with a composition of the invention; a method of coating an electrical device that includes applying a composition of the invention; a method of coating optical fibers that includes applying a composition of the invention; and an article that includes a substrate treated with a composition of the invention.

28 Claims, No Drawings

DEGRADABLE, AMORPHOUS, FLUOROCHEMICAL ACRYLATE POLYMERS

CROSS-REFERENCE TO RELATED APPLICATIONS

This application claims priority to U.S. provisional application Serial No. 60/226,235, filed Aug. 18, 2000.

FIELD OF THE INVENTION

The present invention relates to a novel class of degradable, amorphous fluorochemical acrylate monomers, oligomers, and/or polymers containing pendant branched fluoroalkyl groups that may exhibit low surface energy and improved environmental compatibility.

BACKGROUND OF THE INVENTION

In the art of repellent treatments for substrates, fluorochemicals have found extensive use for nearly half a century as low surface energy materials for imparting repellency to a variety of substrates. For an overview of fluorochemical repellents, see Mason Hayek, Waterproofing and Water/Oil Repellency, 24 Kirk-Othmer Encyclopedia Of Chemical Technology 448–455, 460–462, 3rd ed. (1979).

The treatment of fibrous substrates (e.g., carpets, fabrics, leather, nonwovens and paper) with fluorochemicals to render them repellent to water and oil-based stains and resistant to dry soil has been well documented in the art. Successfully treated with these fluorochemical repellents, such fibrous substrates resist the discoloration that results from normal staining and soiling and thus retain their original aesthetic appeal. A wide variety of such fluorochemical repellents are known and described in the art. Among them are the fluorochemical acrylate polymers disclosed in U.S. Pat. No. 3,341,497 (Sherman et al.) and U.S. Pat. No. 3,462,296 (Raynolds et al.), fluorochemical carbodiimides disclosed in U.S. Pat. No. 3,896,251 (Landucci), fluorochemical esters disclosed in U.S. Pat. No. 3,923,715 (Dettre), U.S. Pat. No. 4,029,585 (Dettre), and U.S. Pat. No. 4,264,484 (Patel) and fluorochemical urethanes and ureas disclosed in U.S. Pat. No. 3,398,182 (Guenthner et al.), U.S. Pat. No. 4,001,305 (Dear et al.), U.S. Pat. No. 4,792,354 (Matsuo et al.) and U.S. Pat. No. 5,410,073 (Kirchner). Commercial fluorochemical repellents of these various types are widely available and are sold, for example, under the SCOTCHGARD and TEFLON trademarks.

Also important is the treatment of hard surface substrates, such as masonry, stone and glass, with repellents to retard the discoloration of the masonry or stone from exposure to water- and oil-based stains and deterioration from spalling and efflorescence. Fluorochemical repellents for masonry and stone are known. U.S. Pat. No. 5,274,159 (Pellerite et al.) describes certain water-soluble or dispersible fluorocarbylalkoxysilane surfactants that may be cured onto a masonry surface. U.S. Pat. No. 6,037,429 (Linert et al.) discloses water-soluble treatments for masonry and stone containing fluorochemical polymers having pendent fluoroaliphatic, carboxyl, (poly)oxyalkylene and optional silyl groups.

In addition to being useful as repellents, fluorochemical polymers have found use as low refractive index coatings for glass optical fibers to help retain the light in the fiber. U.S. Pat No. 5,223,593 (McAllister et al.) describes optical fiber coatings made from homopolymers of 1,1-dihydroperfluorocyclohexylmethyl methacrylate.

Particularly useful as repellents are fluorochemicals containing long chain perfluoroalkyl moieties (i.e., $C_6F_{13}$— to $C_{12}F_{25}$—), as such moieties impart very low surface energy to the substrate surface and thus provide the treated substrate with excellent water and oil repellency. (See, for example, H. C. Fielding, "Organofluorine Compounds and Their Applications," R. E. Banks, Ed., Society of Chemical Industry, p. 214 (1979).) Especially preferred from both cost and performance standpoints are fluorochemical repellents containing primarily straight-chain perfluorooctyl ($C_8F_{17}$—) moieties. It is thought, but not relied upon that such repellents (those containing perfluorooctyl moieties) impart a high degree of repellency to a treated substrate because the perfluoroalkyl groups align to form an ordered, low energy, liquid crystalline-like structure at the substrate surface. This liquid crystalline-like structure, is normally formed by heating the substrate treated with a polymer containing perfluorooctyl moieties, to an elevated temperature, e.g., from about 100° C. to about 150° C., to properly orient the perfluoroalkyl chains.

However, perfluorooctyl group-containing polymers can ultimately degrade to form functional perfluorooctyl-containing compounds. It has been reported that certain functional perfluorooctyl-containing compounds may tend to bio-accumulate in living organisms. This tendency has been cited as a potential concern with regard to some fluorochemical compounds. For example, see U.S. Pat. No. 5,688,884 (Baker et al.).

As a result, there is a desire for new fluorine-containing compounds that can effectively provide water- and oil-repellent properties and can be eliminated more effectively from the body (both the polymer/oligomer and its degradation products). One approach has been to replace the $C_6F_{13}$— to $C_{12}F_{25}$— perfluoroalkyl moieties in the compound with shorter chain analogues (i.e., $C_3$–$C_5$ moieties). For example, U.S. patent application Ser. No. 09/803702 describes water- and oil-repellent urethane oligomers containing at least one pendant $C_4F_9$— repeatable unit and at least one $C_4F_9$— terminal group. Published World Patent Application WO 01/30873 describes fluorochemical sulfonamide polymeric surfactants having at least one pendant group containing a $C_4F_9$— or $C_3F_7$— moiety.

The acrylate monomer $CF_3CF_2CF_2OCF(CF_3)CH(CF(CF_3)_2)(OC(O)CH=CH_2)$ is known. Also known is the acrylate monomer $CF_2CF_2CF_3CH(CF_3)C(O)CH=CH_2$ and its polymers and copolymers. The diacrylate monomer $CH_2=CHC(O)OCH(CF(CF_3)_2)—(CF_2)_8—CH(CF(CF_3)_2)(OC(O)CH=CH_2)$ and its preparation are disclosed in Published World Application WO 00/50517, as well as the conversion of the diacrylate monomer to a polymer by UV curing with a photoinitiator.

SUMMARY OF THE INVENTION

In one aspect, this invention relates to compounds comprising at least one acrylate monomer, said monomer comprising at least one pendant group of the structure —O—CH($R_f$)($R_f'$), wherein $R_f$ is a straight chain or branched perfluoroalkyl group with five or less carbon atoms, and $R_f'$ is a branched perfluoroalkyl group with three to five carbon atoms.

In another aspect, this invention relates to a method of treating a substrate to render it oil-and/or water-repellent comprising treating the substrate with a composition comprising a compound that comprises at least one acrylate monomer, said monomer comprising at least one pendant group of the structure —O—CH($R_f$)($R_f'$), wherein $R_f$ is a straight chain or branched perfluoroalkyl group with five or less carbon atoms, and $R_f'$ is a branched perfluoroalkyl group with three to five carbon atoms.

In still another aspect, this invention relates to a method of reducing the surface tension of a liquid comprising adding to the liquid a compound comprising at least one acrylate monomer, said monomer comprising at least one pendant group of the structure —O—CH($R_f$)($R_f'$), wherein $R_f$ is a straight chain or branched perfluoroalkyl group with five or less carbon atoms, and $R_f'$ is a branched perfluoroalkyl group with three to five carbon atoms.

In yet another aspect, this invention relates to an article comprising a substrate treated with a composition comprising a compound comprising at least one acrylate monomer, said monomer comprising at least one pendant group of the structure —O—CH($R_f$)($R_f'$), wherein $R_f$ is a straight chain or branched perfluoroalkyl group with five or less carbon atoms, and $R_f'$ is a branched perfluoroalkyl group with three to five carbon atoms.

In addition to exhibiting surface energies comparable to known fluorochemical compounds containing pendant straight-chain perfluorooctyl ($C_8F_{17}$—) or perfluorobutyl ($C_4F_9$—) groups, the compounds of this invention containing pendant —O—CH($R_f$)($R_f'$) groups offer two additional advantages. First, the compounds of this invention generally resist hydrolysis under application conditions, possibly due to steric effects caused by the branched fluoroalkyl chain (e.g., in contrast to polymers made by polymerizing $R_fCH_2OC(O)CH=CH_2$, where $R_f$ is a straight chain or branched perfluoroalkyl group). Second, the expected ultimate degradation products of compounds of this invention will generally have minimal adverse environmental effects because these degradation products have a low molecular weight. Oxidation and/or hydrolysis of the compounds will release the fluorinated alcohol or ketone. These ketones have at least 5 carbon atoms and have recently been shown to exhibit low toxicity, in contrast to lower carbon atom-containing perfluoroketones such as $CF_3C(O)CF_3$, which can be very toxic. Furthermore, some perfluorinated ketones of the formula $R_fC(O)R_f'$ and their corresponding alcohols are known to be cleaved by strong bases to form $R_fCOOH$ plus $R_f'H$, suggesting that their environmental lifetimes will be short compared with linear $R_f$ protective groups. This ketone degradation is especially facile when $R_f'$ is $(CF_3)_2CF$—.

Also, due perhaps to the lack of crystallinity of the amorphous branched perfluoroalkyl groups and absence of a clearly defined melt transition temperature, the compounds of this invention do not require curing at elevated temperatures in order to develop their repellent properties and thus can be cured at ambient conditions. In contrast, known polymers containing the core crystalline pendant straight-chain perfluoroalkyl groups (e.g., $C_8F_{17}$— or $C_4F_9$—) require heat treatment to orient the perfluoroalkyl groups properly in order to fully develop their repellent properties.

DETAILED DESCRIPTION OF THE INVENTION

This invention relates to novel amorphous, degradable fluorochemical compounds comprising at least one acrylate monomer comprising polymerizable or a polymer chain of units of the monomer, said compound having at least one pendant group of the structure —O—CH($R_f$)($R_f'$), wherein $R_f$ is a straight chain or branched perfluoroalkyl group with five or less carbon atoms, and $R_f'$ is a branched perfluoroalkyl group with three to five carbon atoms.

The compounds of this invention which are also referred to herein as monomers, oligomers, or polymers of this invention, and fluorochemical acrylate monomers, oligomers, or polymers of the invention can generally be depicted as shown in Formula I:

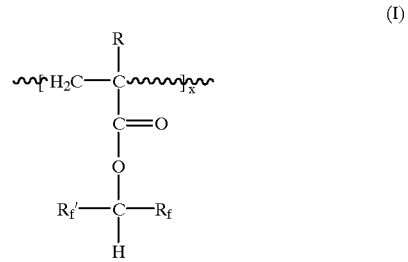

(I)

wherein ~~~ represents a bond in a polymerizable or a polymer chain;

$R_f$ is a straight chain or branched perfluoroalkyl group with five or less carbon atoms;

$R_f'$ is a branched perfluoroalkyl group with three to five carbon atoms;

R is hydrogen, methyl, fluoro or chloro; and x is at least 1.

Preferred monomer compounds are depicted in Formula II:

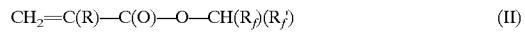

$$CH_2=C(R)—C(O)—O—CH(R_f)(R_f')$$ (II)

wherein

R is hydrogen, methyl, fluoro or chloro; and $R_f$ is a straight chain or branched perfluoroalkyl group with five or less carbon atoms; and $R_f'$ is a branched perfluoroalkyl group with three to five carbon atoms.

Fluorochemical acrylate polymers of this invention contain within the polymer backbone (co)polymerized units having the formula depicted in Formula III:

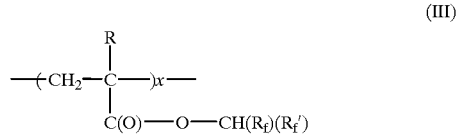

(III)

wherein

R is hydrogen, methyl, fluoro or chloro; and $R_f$ is a straight chain or branched perfluoroalkyl group with five or less carbon atoms;

$R_f'$ is a branched perfluoroalkyl group with three to five carbon atoms; and x is at least 2.

For Formula III, when x has a value from 2 to 10, the fluorochemical acrylate polymer can be considered an oligomer (i.e., a very low molecular weight polymer). Such oligomers are useful as surfactants for coating compositions containing high surface energy organic materials.

For Formula III, when x has a value of greater than 10 and up to about 50, the fluorochemical acrylate polymer is useful as a repellent treatment for fibrous or hard surface substrates and is useful as an optical fiber coating.

For both the acrylate monomers and polymers of this invention, $R_f$ is preferably $CF_3$—, $CF_3CF_2$—, $CF_3CF_2CF_2$—, $(CF_3)_2CF$— or $(CF_3)_2CFCF_2$— and $R_f'$ is either —$CF(CF_3)_2$ or —$CF_2CF(CF_3)_2$. More preferably, $R_f$ is $CF_3CF_2$— or $CF_3CF_2CF_2$— and $R_f'$ is —$CF(CF_3)_2$.

Examples of useful —O—CH($R_f$)($R_f'$) groups include but are not limited to —O—CH($CF_3$)($CF(CF_3)_2$), —O—CH ($CF_2CF_3$)($CF(CF_3)_2$), —O—CH($CF_2CF_2CF_3$)($CF(_3)_2$), —O—CH($CF(CF_3)_2$)$_2$ and —O—CH($CF_2CF(CF_3)_2$)$_2$.

The novel fluorochemical acrylate monomers of this invention can be prepared for example by reacting an alcohol of the formula HO—CH($R_f$)($R_f'$) with an acryloyl compound of the formula $CH_2$=C(R)—C(O)—X in the presence of a tertiary amine acid scavenger, wherein $R_f$, $R_f'$ and R are as defined for Formula II and X is a good leaving group, such as a halogen atom (e.g., Cl or F) or a hydroxyl group. The alcohol can be prepared for example by reduction with sodium borohydride of the corresponding perfluoroketone of the formula $R_f$—C(O)—$R_f'$; see Fokin, A. V., et al.; Bull. Acad. Sci. USSR; EN; 27; 8; 1692–1695 (1978); and Saloutina, L. V. et al; J. Org. Chem. USSR; EN; 18; 685–689 (1982).

The novel fluorochemical acrylate polymers of this invention can be made for example by homopolymerizing or copolymerizing the monomer of Formula II, employing free-radical polymerization techniques well known to one skilled in the art. Useful free-radical initiators include but are not limited to: a persulfate; an azo compound such as azoisobutyronitrile or azo-2-cyanovaleric acid; a hydroperoxide such as cumene, t-butyl, or t-amyl hydroperoxide; a dialkyl peroxide such as di-t-butyl and dicumyl peroxide; a peroxyester such as t-butyl perbenzoate or di-t-butylperoxy phthalate; a diacylperoxide such as benzoyl peroxide; lauroyl peroxide; and the like. The initiating radical formed by the initiator can be incorporated into the fluorochemical acrylate polymer to varying degrees depending on the type and amount of initiator used. A suitable amount of initiator depends on the particular initiator and other reactants being used. About 0.1 percent to about 5 percent by weight of an initiator can be used, based on the total weight of the monomers in the reaction, depending upon the desired molecular weight of the fluorochemical acrylate polymer to be made.

To further control the molecular weight of the polymer, a mono-, di-, or polythiol chain transfer agent can be employed, such as for example ethanethiol, propanethiol, butanethiol, hexanethiol, n-octylthiol, t-dodecylthiol, 2-mercaptoethyl ether, 2-mercaptoimidazole, 2-mercaptoethylsulfide, 2-mercaptoimidazole, 8-mercaptomenthone, 2,5-dimercapto-1,3,4-thiadiazole, 3,4-toluenedithiol, o-, m-, and p-thiocresol, ethylcyclohexanedithiol, p-menthane-2,9-dithiol, 1,2-ethanedithiol, 3-mercapto-1,2-propanediol, 2-mercaptopyrimidine, and the like. The chain transfer agent is generally used in an amount of about 0.025 to about 0.2 equivalents, per equivalent of combined olefinic monomers. When oligomers are desired (i.e., where x in formula I is from 2 to 10) higher levels of chain transfer agent can be employed. The repellent fluorochemical acrylate polymers of this invention are amorphous materials typically having glass transition temperatures ranging from about 0° C. to about 60° C.

In order to achieve the maximum repellent and refractive index properties, it is preferred that the fluorochemical acrylate polymer is a homopolymer of the fluorochemical acrylate monomer of this invention or alternatively is a copolymer of a fluorochemical acrylate monomer of the invention and another fluorine-containing acrylate monomer outside this invention such as for example $CH_2$=CHC(O) OCH($CF_3$)$_2$, or $CH_2$=CHC(O)OCH$_2$CF$_3$. However, small amounts (i.e., up to about 25% by weight) of a fluorine-free comonomer, preferably a comonomer that is non-gaseous under ambient conditions, can be (co)polymerized without significantly degrading the polymer repellency properties. For surfactant applications, higher amounts of fluorine-free comonomer (i.e., up to about 80% by weight) can be (co)polymerized. Useful fluorine-free comonomers include alkyl acrylate esters, vinyl acetate, vinylidene chloride, styrene, alkyl vinyl ethers, alkyl methacrylate esters, acrylic acid, methacrylic acid, acrylamide, methacrylamide, acrylonitrile, methacrylonitrile, and N-vinylpyrrolidone. Alkyl acrylate esters are preferred fluorine-free comonomers and include straight-chain, cyclic, and branched-chain isomers of alkyl esters containing $C_1$–$C_{50}$ alkyl groups. Useful specific examples of alkyl acrylate esters include methyl acrylate, ethyl acrylate, n-propyl acrylate, 2-butyl acrylate, iso-amyl acrylate, n-hexyl acrylate, heptyl acrylate, n-octyl acrylate, iso-octyl acrylate, 2-ethylhexyl acrylate, nonyl acrylate, decyl acrylate, undecyl acrylate, dodecyl acrylate, tridecyl acrylate, and tetradecyl acrylate.

Preferably, the free-radical polymerization is carried out in solvent at any suitable concentration, e.g., from about 5 percent to about 90 percent by weight based on the total weight of the reaction mixture. Examples of suitable solvents include aliphatic and alicyclic hydrocarbons (e.g., hexane, heptane, cyclohexane), aromatic solvents (e.g., benzene, toluene, xylene), ethers (e.g., diethylether, glyme, diglyme, diisopropyl ether), esters (e.g., ethyl acetate, butyl acetate), alcohols (e.g., ethanol, isopropyl alcohol), ketones (e.g., acetone, methyl ethyl ketone, methyl isobutyl ketone), sulfoxides (e.g., dimethyl sulfoxide), amides (e.g., N,N-dimethylformamide, N,N-dimethylacetamide), halogenated solvents (e.g., methylchloroform, FREON™ 113, trichloroethylene, α,α,α-trifluorotoluene, fluorinated ethers such as $C_4F_9OCH_3$, hydrofluorocarbons such as $CF_3CFHCFHCF_2CF_3$, and the like), and mixtures thereof Preferably, the solvent is a low water-solubility solvent such as an ester (e.g., ethyl acetate or butyl acetate), a ketone (e.g., methyl ethyl ketone or methyl isobutyl ketone), or an ether (e.g., diisopropyl ketone).

The polymerization to form the desired polymer can be carried out at any temperature suitable for conducting an organic free-radical reaction. Particular temperature and solvents for use can be easily selected by those skilled in the art based on considerations such as the solubility of reagents, the temperature required for the use of a particular initiator, and the like. While it is not practical to enumerate a particular temperature suitable for all initiators and all solvents, generally suitable polymerization temperatures are between about 30° C. and about 200° C.

For oil- and/or water-repellent applications, compounds of the invention can be most conveniently used as an aqueous composition, in particular an aqueous dispersion in water. If the compound is first made by solution polymerization in a solvent, the polymer or oligomer can subsequently be dispersed in water by vigorously mixing the solution polymer or oligomer with water containing cationic, anionic, amphoteric and/or nonionic surfactants and, if appropriate, other auxiliaries and solvents, employing ultrasonic treatment or treatment in a high pressure homogenizer to provide the energy to form a stable dispersion. A solvent-free dispersion of the compound can then be obtained by subsequent removal via distillation of the polymerization solvent. Generally, the aqueous dispersion as a concentrate contains 5 to 50% by weight of polymer or oligomer, 0.5 to 15% by weight of one or more dispersing and/or emulsifying agents, and 0 to 30% by weight of a solvent or solvent mixture, the remainder being water. Alternatively, the aqueous fluorochemical acrylate polymer or oligomer dispersion may be produced by emulsion polymerization of the fluorochemical acrylate monomer in water in the presence of a cationic, anionic, amphoteric and/or nonionic surfactant, using a water-soluble free-radical initiator such as ammonium persulfate to initiate the polymerization.

Aqueous solutions or dispersions of the fluorochemical acrylate polymers may be topically applied onto any substrate, including fibrous substrates and hard surface substrates to render that substrate resistant to soiling and repellent to water- and oil-based stains. Any topical method of application that produces a uniform thin coating of the polymer on the substrate surface may be employed, such as immersion, flooding, spraying, padding or painting. Once applied from solution or dispersion, the polymer treatment may be dried onto the substrate either under ambient conditions or at elevated temperatures to produce a long-lasting altered surface that does not change the appearance of the substrate. In the case of porous substrates, the penetration of the polymer treatment into the porous substrate surface generally prevents significant adsorption of staining fluids into the substrate (i.e., the fluids will not soak in), even after extensive outdoor exposure, since the coating below the surface is not degraded.

Useful fibrous substrates, which may be protected when topically treated with polymers of this invention, include natural textiles and fabrics such as cotton or wool and synthetic fabrics or textiles such as polyester or nylon, as well as paper and leather(e.g., textiles, carpets, leather, nonwovens, paper). Topical treatment application to fibrous substrates can be accomplished via immersion, spray, foam, kiss roll and metering. For example, the substrate can be immersed in a dispersion or solution of the fluorochemical acrylate polymer and agitated until it is saturated. The saturated fibrous substrate can then be run through a padder/roller to remove excess dispersion, dried in an oven at a relatively low temperature (e.g., at 70° C.) for a time sufficient to remove the dispersion medium (e.g. solvents such as those used in the polymerization reaction), and cured at a temperature and for a time sufficient to provide a cured treated substrate. This curing process can be carried out at temperatures between ambient temperature and about 150° C. depending on the particular composition used. In general, a temperature of about 40 to 150° C. for a period of about 10 minutes is suitable. The cured treated fibrous substrate can be cooled to room temperature and used as desired, e.g., incorporated or fashioned into apparel or upholstery.

Hard surface substrates which may be protected when topically treated with the fluorochemical acrylate polymers of this invention include porous hard surfaces such as masonry (i.e., human-made hard porous materials such as concrete, brick, tile, grout) and stone (i.e., naturally occurring porous materials), substrates used extensively in the construction of buildings, roads, parking ramps, driveways, garage flooring, fireplaces, fireplace hearths, and counter tops. When left unprotected, masonry and stone surfaces quickly discolor from exposure to water- and oil-based stains and gradually deteriorate from spalling and efflorescence induced by water penetration and weather exposure. Protection against discoloration from common water- and oil-based household liquids such as motor oil, brake-oil, transmission fluid, cooking oil, coffee, and wine is highly desirable due to the high cost and labor of replacing such materials. For these massive and immobile substrates, application of treating liquids is most conveniently done by brush, roller or spray and cure must be accomplished at ambient temperature.

The fluorochemical acrylate polymers of this invention may also be used as low refractive index coatings, particularly for coating optical fibers. Typically, optical fibers comprise a light carrying core, for example an inorganic glass such as fused silica or a polymer such as polymethyl methacrylate, and a cladding material having a lower refractive index than the core. By having a lower refractive index, the cladding material serves to confine the light energy within the core and thereby allows propagation of light by a phenomenon generally known as "total internal reflection." Fiber-guided modulated light beams are useful in many applications, for example, telecommunications, computer link-ups, and automotive controls. Advantageously, fiber optic linkages have a greater information carrying capacity as compared to metal wires carrying electrical signals. Furthermore, fiber optics are less likely to suffer from external interference, such as electromagnetic radiation.

The fluorochemical acrylate polymers of this invention can also be employed to apply a coating to an electrical device. Such coating applications include anti-stiction coatings for computer hard drives, barrier coatings to protect sensitive substrates such as circuit boards, and antimigration coatings to prevent the migration of lubricants. Copolymers of the fluorochemical acrylate monomer with for example a small amount of (meth)acrylic acid (i.e., less than 10% by weight, preferably less than 5% by weight) can improve the adhesion of the fluorochemical acrylate polymer to polar substrates such as the metal circuits etched on circuit boards or the metallic surfaces of computer hard drives or optical pellicle frames.

The amount of the fluorochemical compound applied to a substrate in accordance with this invention is chosen so that desirably high surface modification (e.g., water and/or oil repellency, refractive index reduction) is imparted to the substrate surface, said amount usually being such that 0.01% to 5% by weight, preferably 0.05 to 2% by weight, of fluorine is present on the treated substrate. The amount, which is sufficient to impart desired repellency or refractive index reduction, can be determined empirically and can be increased as necessary or desired.

The fluorochemical acrylate polymers of this invention are also useful as surfactants for lowering the surface tension of liquids and thus can be employed to improve the wetting properties of coating compositions containing high surface energy organic materials. Such "difficult-to-wet-with" materials include thermoset resins (e.g., high solids formulations containing epoxy resins, acrylic resins, aminoplasts and/or polyols) and thermoplastic resins (e.g., plasticized polyvinyl chloride dispersions). Particularly useful as surfactants are copolymers of the fluorochemical acrylate monomers of this invention with polyoxyalkylene acrylate esters, such as the acrylate esters of PLURONIC™ propylene oxide/ethylene oxide copolymers (copolymers available from BASF Corp., Mount Olive, N.J.) or the acrylate esters of CARBOWAX™ polyethylene glycols (glycols available from Union Carbide Corp., South Charleston, W. Va.). An effective use level for the surfactants is at least 0.1%, preferably at least 0.2%, and more preferably at least 0.5% by weight of the high surface energy organic material.

EXAMPLES

Objects and advantages of this invention are further illustrated by the following examples, but the particular materials and amounts thereof recited in these examples, as well as other conditions and details, should not be construed to unduly limit this invention. Unless otherwise specified, all percentages and proportions are by weight.

Test Methods

The test methods used to evaluate the performance described in the later-described Examples and Comparative Examples are described below.

Glass Transition Temperature (Tg)—For each glass transition temperature determination, the sample used consisted of polymer solids obtained by removing the solvent from the polymer solution by drying the solution in a forced air oven at 100° C. for at least 30 minutes. The glass transition temperature (Tg) of each sample was determined by Differential Scanning Calorimetry using a Perkin-Elmer 7-Series Thermal Analysis System (Perkin-Elmer Corp., Norwalk, Conn.) with a general temperature range of −50 to 200° C. Tg values were determined according to ASTM protocol E1356-91 except a 20° C./minute ramp was used. If a transition could not be found in the general range, the temperature range was expanded as needed. Measurements were made after two heat and cool cycles. The Tg was recorded as a midpoint determination of the point at which the derivative of the interpolated slope of the transition equaled zero.

Advancing and Receding Contact Angle Test—The Advancing and Receding Contact Angle Test provides a quick and precise prediction of the surface properties of a coating material. Advancing and Receding contact angle values measured with water and n-hexadecane using this test have correlated well with fluid repellency values measured on fabrics and carpets.

To run this test, a solution, emulsion, or suspension (typically at about 3% solids) is applied to a polymer film (nylon or polyester) by dip-coating. The polymer film is prepared as follows. Polymer film is cut into 85 mm×13 mm rectangular strips. Each strip is cleaned by dipping into methyl alcohol, wiping with a KIMWIPE™ wiper (commercially available from Kimberly-Clark Corp., Neenah, Wis.), taking care not to touch the strip's surface, and allowing the strip to dry for 15 minutes. Then, using a small binder clip to hold one end of the strip, the strip is immersed in the treating solution, and the strip is withdrawn slowly and smoothly from the solution. The coated film strip is tilted to allow any solution run-off to accumulate at the corner of the strip, and a KIMWIPE™ wiper is touched to the corner to pull away the solution buildup. The coated film strip is allowed to air dry in a protected location for a minimum of 30 minutes and then cured for 10 minutes at 121° C. unless otherwise indicated.

After the treatment is dry and cured, the advancing and receding contact angles are measured using a CAHN Dynamic Contact Angle Analyzer, Model DCA 322 (a Wilhelmy balance apparatus equipped with a computer for control and data processing, commercially available from ATI, Madison, Wis.). The CAHN Dynamic Contact Angle Analyzer is calibrated using a 500 mg weight. An alligator clip is fastened to a piece of coated film strip about 30 mm long, and the clip and film piece are hung from the stirrup of the balance. A 30 mL glass beaker containing approximately 25 mL of water or n-hexadecane is placed under the balance stirrup, and the beaker is positioned so that the coated film strip is centered over the beaker and its contents but not touching the walls of the beaker. Using the lever on the left side of the apparatus, the platform supporting the beaker is carefully raised until the surface of water or n-hexadecane is 2–3 mm from the lower edge of the film strip. The door to the apparatus is closed, the "Configure" option is chosen from the "Initialize" menu of the computer, the "Automatic" option is chosen from the "Experiment" menu, and the computer program then calculates the time for a scan. The apparatus then raises and lowers the liquid so that the scan is taken (the advancing angle is measured as the liquid moves up and over the surface, while the receding angle is determined as the liquid moves down and away from the surface of the plastic film). The "Least Squares" option is then selected from the "Analysis" menu, and the average receding contact angle is calculated from the scan of the film sample. Three separate films are prepared for each material to be tested as previously described. The 95% confidence interval for the average of the 3 scans is typically about 1.2°. This procedure is repeated for water and n-hexadecane.

Surface Tension Measurement—All surface tension measurements for the polymeric surfactants were made using a Krüss K-12 Tensiometer integrated with an automatic dosimat and a computer equipped with a K121 software package (available from Krüss U.S.A, Charlotte, N.C.). The program was run using a Wilhelmy platinum plate (PL 12) and glass sample vessel (GL7).

Preparation of Compounds

Polymer 1. Preparation of $CH_2=CHC(O)—O—CH(CF_3)(CF(CF_3)_2)$ Homopolymer

Perfluoro(methyl isopropyl ketone) (64 g, 0.24 mol, can be prepared as described in Example 5 of World Published Application WO 01/05468) was reduced to the corresponding alcohol with $NaBH_4$ (10.9 g, 0.29 mol, available from Sigma-Aldrich Chemical Co., Milwaukee, Wis.) in 235 mL anhydrous diglyme (anhydrous diethylene glycol dimethyl ether, available from Sigma-Aldrich Chemical Co.) at approximately 0° C. The reaction mixture was quenched with cold 10% aqueous HCl (200 mL). The lower phase was isolated, washed twice with 200 mL aliquots of saturated NaCl solution at 0° C., dried over anhydrous $MgSO_4$ and filtered to give a filtrate (80.7 g). The solvent was distilled from the filtrate to produce 56.7 g of 1,1,1,3,4,4,4-heptafluoro-3-(trifluoromethyl)-2-butanol with a yield of 88% (b.p.=100–140° C.). Analysis by proton and fluorine NMR showed the following peaks: −72.5(3F), −75.5(3F), −74.3(3F), −182.7(1F), 4.6 (1H), 3.8 (1H).

25.7 g (0.096 mol) of the 1,1,1,3,4,4,4-heptafluoro-3-(trifluoromethyl)-2-butanol was dissolved in diglyme (50 ml) and the resulting solution was cooled to 5° C. under a nitrogen blanket. Acryloyl chloride (9.5 g, 0.105 mol, available from Sigma-Aldrich Chemical Company) was added to this solution by syringe while stirring. To this solution was added diisopropylethyl amine (13.6 g, 0.105 mol, available from Sigma-Aldrich Chemical Co.) dropwise over a period of 35 minutes. After 2 hours, the reaction mixture was filtered to remove the solid by-products and the filtrate was diluted with methylene chloride (40 mL). The filtrate was then washed three times with 75 mL aliquots of saturated NaCl solution, dried over anhydrous $MgSO_4$, filtered, and the solvent removed by rotary evaporation to leave a residue of 22 g of crude acrylate ester. The acrylate ester was purified via column chromatography using silica gel to produce 16.2 g of purified ester. Fluorine NMR analysis showed the following peaks: −74.3 (3F), −75.5(3F), −182.7 (1F), −72.4(3F). Proton NMR analysis showed the following peaks: 6.15 (1H), and 3 olefinic hydrogens at 6.6, 6.2, and 6.1 ppm.

The purified acrylate ester (5.5 g, 0.017 mol) and VAZO™ 64 initiator (28 mg) was then dissolved in 30 g of ethyl acetate in a 4 oz (110 g) polymerization bottle. The solution was purged for 90 seconds using $N_2$ at 1 L/min, then polymerization was affected by heating the solution for 26 hours by rotating the bottle in a heated water bath. After the polymerization, the solvent was removed by rotary evaporation. The resulting yellow oil was twice dissolved in acetone and precipitated from solution with chloroform. The resulting solid was collected by filtration and dried. The structure of the homopolymer was verified by proton and fluorine NMR. Tg was 53.9° C. with onset at 27.7° C. The solid collected by filtration was dissolved at 3% solids in $C_4F_9OCH_3$ (available as HFE-7100 Engineering Fluid from 3M Company, St. Paul, Minn.).

Polymer 2. Preparation of $CH_2=CHC(O)—O—CH(CF_2CF_3)(CF(CF_3)_2)$ Homopolymer

Perfluoro(ethyl isopropyl ketone) (151 g, can be prepared as described in Example 1 of World Published Application WO 01/05468) was slowly added to a stirred mixture of 14.0 g $NaBH_4$ in 150 mL anhydrous tetraglyme (available from Sigma-Aldrich Chemical Co., Milwaukee, Wis.), controlling the exotherm with an ice bath. Cautious workup with about 100 mL methanol and then about 300 mL 5% aqueous HCl, followed by extraction with $C_4F_9OCH_3$ and distillation, yielded 129.6 g $C_2F_5CH(OH)CF(CF_3)_2$ (b.p. 88° C.).

A solution containing 61.5 g of the resulting alcohol and 14.5 g N,N-diisopropylethyl amine (available from Sigma-Aldrich Chemical Co.) in 150 mL methylene chloride was treated with 9.5 g acryloyl chloride (available from Sigma-Aldrich Chemical Co.). After washing with 5% aqueous sulfuric acid, the reaction product was treated with a small amount of phenothiazine (available from Sigma-Aldrich Chemical Co.), concentrated, and distilled at 30° C. and approximately 5 torr to provide a main acrylate ester monomer cut. The recovered monomer had a refractive index of 1.3186 measured at 21.3° C. For comparison, the refractive index of $C_7F_{15}CH_2OC(O)CH=CH_2$, a monomer interpolymerized in low refractive index polymer used for coating glass optical fibers, had a slightly higher measured refractive index of 1.3289. (Low refractive indexes are preferred.)

10.0 g of the resulting acrylate ester monomer was mixed with 30 g ethyl acetate (EtOAc) in a 4 oz (110 g) bottle and was polymerized using 100 mg VAZO™ 64 initiator (2,2'-azobisisobutyronitrile, available from E. I. duPont de Nemours & Co., Wilmington, Del.). The resulting solution was purged for 35 seconds using $N_2$ at 1 L/min, then heated for 22 hours by rotating the bottle in a heated water bath set at 60° C. The polymer that precipitated during the reaction (3.2 g, Tg=33° C.) was separated and dissolved at 3% solids in $C_4F_9OCH_3$.

Polymer 3. Preparation of $CH_2=CHC(O)—O—CH(C_3F_7)(CF(CF_3)_2)$ Homopolymer $C_3F_7CH(OH)CF(CF_3)_2$ (where $C_3F_7$ represents an approximately 45/55 blend of n-$C_3F_7$ and i-$C_3F_7$) was prepared by reduction of the corresponding ketone, $C_3F_7C(O)CF(CF_3)_2$ (can be prepared as described in Example 3 of World Published Application WO 01/05468), using the borohydride reduction procedure described in the preparation of Polymer 2. The resulting alcohol was converted to the corresponding acrylate ester monomer by esterification with acryloyl chloride, also described in the preparation of Polymer 2 (b.p. 38–60° C. at 15 torr).

A homopolymer acrylate was then prepared by homopolymerizing 10.0 g acrylate ester monomer in 30 g EtOAc using 76 mg VAZO™ 64 initiator. The resulting precipitated homopolymer had a Tg of 11° C. The homopolymer was dissolved at 3% solids in $C_4F_9OCH_3$.

Polymer 4. Preparation of $CH_2=CHC(O)—O—CH(CF(CF_3)_2)_2$ Homopolymer

Perfluoro(diisopropyl ketone)(96.5 g, 0.26 mol, can be prepared as described in Example 5 of World Published Application WO 01/05468) was reduced to the corresponding alcohol, $[(CF_3)_2CF]_2CHOH$, by reacting the ketone with $NaBH_4$ (11 g, 0.29 mol) in 250 mL of anhydrous diglyme (anhydrous diethylene glycol dimethyl ether, available from Sigma-Aldrich Chemical Co.) at approximately 0° C. The reaction mixture was quenched with cold 10% aqueous HCl (250 mL). The mixture was washed with 250 mL of 10% aqueous HCl and 250 mL of saturated NaCl solution (at approximately 0° C.), dried over anhydrous $MgSO_4$, and filtered. The filtrate was distilled to produce 81.6 g of 1,1,1,2,4,5,5,5-octafluoro-2,4-bis-trifluoromethyl-pentan-3-ol (b.p.=112–114° C.). Analysis by proton and fluorine NMR (neat fluid+$CFCl_3$ & TMS) showed the following peaks: −71.0 (6F), −76.7(6F), −182.4(2F), 5.3 (1H, quartet), 6.5 (1H, doublet).

The alcohol was esterified to the corresponding acrylate monomer by reaction with acryloyl chloride in the presence of triethylamine (boiling range=42–44° C. at 14 torr). The fluorochemical acrylate homopolymer was then prepared by polymerizing 5.0 g fluorochemical acrylate monomer using 0.05 g VAZO™ 64 initiator in 50 mL ethyl acetate. The homopolymer was precipitated from the ethyl acetate solution, filtered, washed with fresh ethyl acetate, and dried. The dried polymer was dissolved at 3% solids in $C_4F_9OCH_3$.

Polymer 5. Preparation of $CH_2=CHC(O)—O—CH(CF_2CF(CF_3)_2)_2$ Homopolymer

Direct fluorination of 624.2 g (3.35 mol) 2,6-dimethyl-4-heptyl acetate (made by reacting 2,6-dimethyl-4-heptanol (available from Sigma-Aldrich Chemical Co.) and acetyl chloride, b.p.=40–46° C. at 1 torr) in perfluoro-N-methylmorpholine solvent was conducted in a tubular reactor at 35° C., as described in U.S. Pat. No. 5,578,278. The solvent was removed by distillation to leave 1583.5 g of opaque tan liquid, shown by gas-liquid chromatography (glc) to contain primarily two main components, 31% perfluoro-2,6-dimethyl-4-heptanone and 53% 4H-perfluoro-(2,6-dimethyl-4-heptyl)trifluoroacetate). The tan liquid was filtered and distilled to yield a series of fractions boiling from 110° C./745 torr to 90° C./40 torr, with the ketone predominant in the initial fractions. The initial fractions were recombined to form a mixture containing approximately 419 g (0.88 mol) ketone and 764 g (1.35 mol) trifluoroacetate, for an overall yield of 67% of crude product. 4H-perfluoro-2,6-dimethyl-4-heptanol was prepared from this ketone-containing mixture and mixtures prepared in a similar fashion by using several methods. The first method employed treatment of 1305 g of crude ketone product with 200 mL 14% $BF_3$ in methanol (available from Sigma-Aldrich Chemical Co.) at ice temperature, quenching the product in water, and distilling the product to give 664 g of alcohol (b.p.=140–170° C.). Alternatively, a mixture containing 530 g of a distillate containing 32% ketone-64% 4H ester and 300 g 25% aqueous NaOH was vigorously stirred at 70° C. for 18 hours, acidified with 25% aqueous sulfuric acid and distilled to give 233 g of alcohol (b.p.=140–150° C.). In a preferred alternative, 246 g of a distillate containing 58% ketone–30% 4H ester was reduced with 13.8 g $NaBH_4$ to give 208 g of alcohol (b.p.=138–146° C.). This alcohol proved unreactive to trifluoroacetic anhydride, which is indicative of extreme steric hindrance about the hydroxyl group.

A mixture consisting of 501.2 g distilled alcohol, 96.4 g acryloyl chloride, 150 mL CFC-113, and 150 mL methylene chloride was cooled using ice and treated dropwise with 107 g triethylamine (available from Sigma-Aldrich Chemical Co.). The reaction mixture was worked up as described in Polymer 2 to provide 426 g acrylate ester monomer (b.p.=

55–60° C. at 1.2 torr). A mixture of 10 g acrylate ester monomer, 25 g EtOAc, and 75 mg VAZO™ 64 initiator was heated for 24 hours using a steam bath at 60–70° C. to give an insoluble polymer that dried to a brittle white solid (Tg=36° C.; TGA (air): 10% loss at 300° C., 50% loss at 350° C.). The dried polymer was dissolved at 3% solids in $C_4F_9OCH_3$.

Polymer 6. Preparation of $CH_2=CHC(O)OCH(CF_3)_2$ Homopolymer

To a 4 oz (110 g) narrow mouth amber bottle were added 10 g of 1,1,1,3,3,3-hexafluoroisopropyl acrylate ($CH_2=CHC(O)OCH(CF_3)_2$, 99% pure, refractive index of 1.3190 at 20° C., available from Fluorochem USA, West Columbia, S.C.), 0.05 g of VAZO™ 64 initiator and 40 g of $C_4F_9OCH_3$. The bottle and contents were purged with nitrogen gas for approximately one minute, then the bottle was capped securely. The bottle and contents were then tumbled in a constant temperature water bath at 65° C. for 18 hours. After the polymerization, the reaction mixture was diluted to 3% concentration with $C_4F_9OCH_3$.

Polymer 7. Preparation of $CH_2=CHC(O)OC_2H_4O(CF_3)=C(CF(CF_3)_2)_2$ Homopolymer Into a flask equipped with stirrer and heater was placed 18.0 g hexafluoropropylene trimer (available from Lancaster Synthesis, Inc., Windham, N.H.), 4.05 g triethylamine and 30 mL tetrahydrofuran. To this mixture was slowly added 4.8 g 2-hydroxyethyl acrylate (available from Sigma-Aldrich Chemical Co.). The resulting two phase system was heated to about 45° C. and became a single phase after 20 minutes, indicating the end of the reaction. The reaction product was dissolved in 1,1,2-trifluoro-1,2,2-trichloroethane, washed with water, and distilled from phenothiazine to yield the monomer $CH_2=CHC(O)OC_2H_4O(CF_3)=C(CF(CF_3)_2)_2$, a yellow liquid boiling at 84–85° C./0.6 torr.

Following the general procedure described for the preparation of Polymer 5, a polymer was made by homopolymerizing 5 g of $CH_2=CHC(O)OC_2H_4O(CF_3)=C(CF(CF_3)_2)_2$ monomer in 26.4 g EtOAc for 24 hours at 60° C. using 37 mg of VAZO™ 64 initiator, resulting in a clear solution. The polymer was precipitated from solution using methyl alcohol, a sample was dried, and the measured Tg was 45° C. The remaining polymer was then dissolved in 1,1,2-trifluoro-1,2,2-trichloroethane to form a clear solution.

Polymer 8. Preparation of $CH_2=CHC(O)—O—CH(CF_3)(C_6F_{13})$ Homopolymer 100 g perfluoro(2-octanone) (can be prepared as described in Example 4 of World Published Application WO 01/05468) in 100 g perfluorohexane (available as FLUORINERT™ FC-72 from 3M Co.) was reduced over 0.82 g of 10% Pd/C catalyst (available from Sigma-Aldrich Chemical Co.) in a low-pressure Parr hydrogenator, as measured by rapid uptake of $H_2$. Distillation provided 78.9 g of the alcohol (b.p. 128–130 ° C.). 20.9 g of this alcohol was converted to 19.5 g acrylate ester monomer as described for Polymer 1 (b.p.=93° C. at 63 torr, refractive index=1.3172 at 23° C.). A mixture of 10.0 g acrylate ester monomer, 30 g EtOAc, and 100 mg VAZO™ 64 initiator was heated for 24 hours using a steam bath at 60° C. to give 7.2 g of an insoluble polymer that dried to a brittle white solid (Tg=11° C.). The dried polymer was dissolved at 3% solids in $C_4F_9OCH_3$.

Polymer 9. Preparation of $C_8F_{17}SO_2N(C_2H_5)C_2H_4OC(O)CH=CH_2$ Homopolymer To an 8 ounce (220 g) narrow mouth amber bottle were added 20 g of $C_8F_{17}SO_2N(C_2H_5)C_2H_4OC(O)CH=CH_2$ ("MeFOSEA" monomer, can be prepared using the general procedure described in U.S. Pat. No. 2,803,615), 0.2 g of VAZO™ 64 initiator and 80 g of $C_4F_9OCH_3$. The bottle was purged with nitrogen gas for approximately one minute, then capped securely. The bottle and its contents were then tumbled in a constant temperature water bath at 65° C. for 18 hours. The reaction mixture was diluted to 3% solids in $C_4F_9OCH_3$ before testing.

Polymer 10. Preparation of $C_8F_{17}CH_2CH_2OC(O)CH=CH_2$ Homopolymer

Essentially the same procedure was followed as described for the synthesis of Polymer 9, except that 20 g of $C_8F_{17}CH_2CH_2OC(O)CH=CH_2$ ("FOEA" monomer, can be prepared by reacting ZONYL™ BA alcohol (available from E. I. duPont de Nemours & Co., Wilmington, Del.) with acryloyl chloride) was substituted for 20 g of MeFOSEA monomer.

Polymer 11. Preparation of 75/25 $C_8F_{17}SO_2N(CH_3)C_2H_4OC(O)CH=CH_2/C_4H_9OC(O)CH=CH_2$ Copolymer Essentially the same procedure was followed as described for the synthesis of Polymer 9, except that 5 g of n-butyl acrylate (available from Sigma-Aldrich Chemical Co.) was substituted for 5 g (one quarter) of the MeFOSEA monomer.

Polymer 12. Preparation of $C_8C_{17}SO_2N(C_4H_9)C_2H_4OC(O)CH=CH_2$ Homopolymer Essentially the same procedure was followed as described for the synthesis of Polymer 9, except that 20 g of $C_8F_{17}SO_2N(C_4H_9)C_2H_4OC(O)CH=CH_2$ ("BuFOSEA" monomer, available as FLUORAD™ FX-189 intermediate from 3M Company) was substituted for 20 g of MeFOSEA monomer.

Polymer 13. Preparation of 98.8/1.2 $CH_2=CH—C(O)—O—CH(C_2F_5)(CF(CF_3)_2)$/AA Copolymer Into a flask equipped with an overhead stirrer, a thermocouple and an addition funnel was placed 25 g (0.067 mol) of 1-pentafluoroethyl-2-(trifluoromethyl)-2,3,3,3-tetrafluoropropyl acrylate ester, 0.3 g (0.0042 mol) of acrylic acid (AA, available from Sigma-Aldrich Chemical Co.), 143 g of $C_4F_9OC_2H_5$ (available as NOVEC™ HFE-7200 engineering fluid from 3M Company) and 1.01 g of LUPEROX™ 26-M50 initiator (50% solution in mineral spirits, available from Elf Atochem North America, Philadelphia, Pa.). The resulting solution was degassed several times using a nitrogen stream, and the polymerization was carried out at 73° C. for 16 hours. The resulting polymer was completely soluble in $C_4F_9OC_2H_5$ so the reaction solution was poured into methanol, causing the polymer to precipitate. The precipitate was separated, air dried and subsequently redissolved in $C_4F_9OCH_3$ to give an 8.3% solids solution. The solution was further diluted with $C_4F_9OCH_3$ to give a 3% solids solution. The Tg for this polymer was 16° C.

The 1-pentafluoroethyl-2-(trifluoromethyl)-2,3,3,3-tetrafluoropropyl acrylate ester was prepared from the alcohol by reacting the alcohol with acryloyl chloride using a tertiary amine catalyst, N,N-diisopropylethyl amine, as described for Polymer 1

The 1-pentafluoroethyl-2-(trifluoromethyl)-2,3,3,3-tetrafluoropropyl alcohol was prepared as follows. Into a flask equipped with an overhead stirrer, a thermocouple and an addition funnel were placed 53.9 g (1.47 mol) of $NaBH_4$ and 500 mL of tetraethylene glycol diethyl ether. The resulting mixture was cooled to under 10° C., and 37.5 g (1.19 mol) of 1,1,1,2,4,4,5,5,5-nonafluoro-2-trifluoromethyl-pentan-3-one was added over approximately a four hour period, keeping the reaction mixture temperature under 17° C. The reaction mixture was then stirred for 1 hour, allowing the temperature to warm to 15° C. The reaction mixture was then cooled back down to 5° C. using an ice bath, and 10% aqueous HCl was added in two 250 mL aliquots, adding the aqueous acid slowly over a 2 hour time period to minimize foaming. Next, an additional 400 mL of 10% aqueous HCl was added to completely dissolve the solids. The mixture was transferred to a 2-L separatory funnel and the clear lower phase was saved. The upper aqueous phase was then extracted with a 200 mL aliquot of perfluorohexane and was combined with the lower phase. The residual water was removed by distillation with a Dean Stark trap with return. The resulting 1-pentafluoroethyl-2-(trifluoromethyl)-2,3,3,3-tetrafluoropropyl alcohol product was distilled at 98° C. to obtain 303.5 g of product (80% yield).

The precursor 1,1,1,2,4,4,5,5,5-nonafluoro-2-trifluoromethyl-pentan-3-one, $CF_3CF_2C(O)CF(CF_3)_2$, was prepared as follows. Into a clean dry 600 mL Parr reactor equipped with a stirrer, a heater and a thermocouple were added 5.6 g (0.10 mol) of anhydrous potassium fluoride and 250 g of anhydrous diglyme. The anhydrous potassium fluoride used in this synthesis was spray dried, stored at 125° C. and ground shortly before use. The contents of the reactor were then stirred while 21.0 g (0.13 mol) of $C_2F_5COF$ (approximately 95.0% purity) was added to the sealed reactor. The reactor and its contents were then heated, and once a temperature of 70° C. was reached, a mixture of 147.3 g (0.98 mol) of $CF_2=CFCF_3$ (hexafluoropropylene) and 163.3 g (0.98 mol) of $C_2F_5COF$ was added over a 3.0 hour time period. During the addition of the hexafluoropropylene and the $C_2F_5COF$ mixture, the pressure was maintained at less than 95 psig (7500 torr). The pressure at the end of the hexafluoropropylene addition was 30 psig (2300 torr) and did not change over the 45-minute hold period. The reactor contents were allowed to cool and were one-plate distilled to obtain 307.1 g containing 90.6% 1,1,1,2,4,4,5,5,5-nonafluoro-2-trifluoromethyl-pentan-3-one and 0.37% $C_6F_{12}$ (hexafluoropropylene dimers) as determined by gas chromatography. The crude fluorinated ketone was water-washed, distilled, and dried by contact with silica gel to provide a fractionated fluorinated ketone of 99% purity that contained 0.4% hexafluoropropylene dimers.

Polymer 14. Preparation of 98.8/1.2 $CH_2=CH—C(O)—O—CH(C_2F_5)(CF(CF_3)_2)$/MAA Copolymer Polymer 14 was prepared using essentially the same procedure as described for the preparation of Polymer 13. In this case, 23.8 g (0.064 mol) of 1-pentafluoroethyl-2-(trifluoromethyl)-2,3,3,3-tetrafluoropropyl acrylate (monomer prepared as described for Polymer 13) and 0.33 g (0.0038 mol) of methacrylic acid (MAA, available from Sigma-Aldrich Chemical Co.) were copolymerized in 136 g of $C_4F_9OC_2H_5$ using LUPEROX™ 26-M50 initiator (0.96 g of 50% solution in mineral spirits) by heating at 73° C. for 16 hours. The resulting copolymer was precipitated from solution in $C_4F_9OC_2H_5$ by addition of methanol. The precipitate was isolated by decantation, air-dried and then dissolved at 11.9% solids in $C_4F_9OCH_3$. The resulting solution was further diluted to 3% solids with additional $C_4F_9OCH_3$ before testing. The resulting copolymer had a Tg of 2.3° C.

Polymer 15. Preparation of 25/75 $CH_2=CH—C(O)—O—CH(CF_2CF_3)(CF(CF_3)_2)$/PLURONIC™ L-44 Acrylate Copolymer Into a 1-L, 3-necked round bottom flask equipped with an overhead stirrer, a water condenser, a thermocouple and a source of dry nitrogen were added $CH_2=CHC(O)—O—CH(CF_2CF_3)(CF(CF_3)_2)$ (30 g), PLURONIC™ L-44 acrylate (140 g, about 63% solids in toluene) (theoretically $HO(CH_2CH_2O)_{11}[CH(CH_3)CH_2O]_{21}(CH_2CH_2O)_{11}C(O)CH=CH_2$), can be prepared as described in Example 1 of U.S. Pat. No. 3,787,351), VAZO™ 64 initiator (3.6 g), 3-mercapto-1,2-propanediol chain transfer agent (7.2 g, available from Sigma-Aldrich Chemical Co.) and toluene (194 g). The resulting solution was de-gassed several times using dry nitrogen and was then heated to 79° C. with stirring. After a brief exotherm to 84° C., the temperature was maintained at 79° C. for 6 hours. The toluene was then removed from the polymer reaction product using rotary evaporation at 55° C. and water aspirator vacuum to yield 111 g of polymeric surfactant product.

Polymer 16. Preparation of 25/75 $CH_2=CH—C(O)—O—CH(CF_2CF_2CF_3)(CF(CF_3)_2)$/PLURONIC™ L-44 Acrylate Copolymer Into a 1-L, 3-necked round bottom flask equipped with an overhead stirrer, a water condenser, a thermocouple and a source of dry nitrogen were added $CH_2=CHC(O)—O—CH(CF_2CF_2CF_3)(CF(CF_3)_2)$ (10 g), PLURONIC™ L-44 acrylate (46.7 g, about 63% solids in toluene), VAZO™ 64 initiator (1.2 g), 3-mercapto-1,2-propanediol chain transfer agent (2.4 g) and toluene (65 g). The resulting solution was de-gassed several times using dry nitrogen and was then heated to 79° C. with stirring for 6 hours. The toluene was then removed from the polymer reaction product using rotary evaporation at 55° C. and water aspirator vacuum to yield 45 g of polymeric surfactant product.

Polymer 17. Preparation of 22/78 $C_4F_9SO_2N(CH_3)C_2H_4OC(O)CH=CH_2$/PLURONIC™ L-44 Acrylate Copolymer This copolymer can be prepared using the procedure described in Example 4 of World Published Patent Application WO 01/30873.

Polymer 18. Preparation of 99/1 $CH_2=CHC(O)—O—CH(CF_2CF(CF_3)_2)_2$/AA Copolymer Following the general procedure described for the preparation of Polymer 5, 9.9 g $CH_2=CHC(O)—O—CH(CF_2CF(CF_3)_2)_2$ was copolymerized with 0.1 g acrylic acid in 30 g EtOAc for 22 hours at 60° C. using 75 mg VAZO™ 64 initiator. No performance evaluations were conducted with this copolymer.

Polymers 19–21. Preparation of $CH_2=CHC(O)—O—CH(CF_2CF(CF_3)_2)_2$/VCl$_2$ Copolymers Following the general procedure described for the preparation of Polymer 5, a series of copolymers, Polymer 19, 20 and 21, were made by copolymerizing $CH_2=CHC(O)—O—CH(CF_2CF(CF_3)_2)_2$ (FC monomer) with vinylidene chloride (VCl$_2$, available from Sigma-Aldrich Chemical Co.) in 40 g EtOAc for 22 hours at 60° C. using 150 mg of VAZO™ 64 initiator.

The following amounts of each monomer were used to make each copolymer:

Polymer 19: 16 g FC monomer, 4 g VCl$_2$ (80/20 copolymer)

Polymer 20: 18 g FC monomer, 2 g VCl$_2$ (90/10 copolymer)

Polymer 21: 19 g FC monomer, 1 g VCl$_2$ (95/5 copolymer)

For Polymer 20, the measured Tg was 37.8° C.

Examples 1–5

Glass transition temperatures (Tg) and advancing and receding contact angles (ACA and RCA) vs. water and n-hexadecane (n-$C_{16}H_{34}$) were measured for Polymers 1–5, several fluorochemical homopolymers of this invention containing pendant —O—CH($R_f$)($R_f'$) groups. Each homopolymer was coated onto polyester film from a 3% solids polymer solution in either $C_4F_9OCH_3$ (available as NOVEC™ HFE-7100 engineering fluid from 3M Company, St. Paul, Minn.) or α,α,α-trifluorotoluene (available from Sigma-Aldrich Chemical Co., Milwaukee, Wis.). The coated film was then cured for 24 hours at ambient temperature prior to contact angle testing.

Results are presented in TABLE 1; the $R_f$ and $R_f'$ group is indicated for each homopolymer.

TABLE 1

| Ex. | Polymer | $R_f$ | $R_f'$ | Tg, °C. | Water: ACA | Water: RCA | n-Hexadecane: ACA | n-Hexadecane: RCA |
|---|---|---|---|---|---|---|---|---|
| 1 | 1 | $CF_3$— | $(CF_3)_2CF$— | 54 | 118 | 73 | 68 | 49 |
| 2 | 2 | $C_2F_5$— | $(CF_3)_2CF$— | 33 | 118 | 98 | 69 | 62 |
| 3 | 3 | n-$C_3F_7$—, i-$C_3F_7$— | $(CF_3)_2CF$— | 11 | 117 | 97 | 68 | 63 |
| 4 | 4 | $(CF_3)_2CF$— | $(CF_3)_2CF$— | N/R* | 115 | 79 | 68 | 60 |
| 5 | 5 | $(CF_3)_2CFCF_2$— | $(CF_3)_2CFCF_2$— | 41 | 118 | 103 | 70 | 63 |

* N/R = not run

Examining the data in TABLE 1, the high advancing water contact angles and generally high receding water contact angles are unexpected for a polymer containing short branched fluoroaliphatic groups. Good advancing and receding contact angles vs. n-hexadecane are also exhibited by polymers of this invention.

Examples 6–7

To determine the effect of cure temperature on the repellent performance of polymers of this invention, advancing and receding contact angles against n-hexadecane and water were measured for Polymer 5, the homopolymer of $CH_2=CHC(O)$—O—$CH(CF_2CF(CF_3)_2)_2$, at 25° C. (i.e., ambient cure) and at 150° C. (i.e., forced air oven cure Again, each polymer was coated onto polyester film from a 3% solids polymer solution in either $C_4F_9OCH_3$ or α,α,α-trifluorotoluene.

Results from these evaluations are presented in TABLE 2.

TABLE 2

| Ex. | Polymer | Cure Temp. (° C.) | Water: ACA | Water: RCA | n-Hexadecane: ACA | n-Hexadecane: RCA |
|---|---|---|---|---|---|---|
| 6 | 5 | 25 | 119 | 100 | 70 | 62 |
| 7 | 5 | 150 | 116 | 100 | 70 | 62 |

The data in TABLE 2 show that cure temperature has no effect on water and hexadecane contact angles. This is believed to be due to the amorphous nature of the fluoroacrylate polymer. In contrast, conventionally used fluoroacrylate polymers having $C_8F_{17}$— crystalline side chains, such as homopolymers of $C_8F_{17}SO_2N(CH_3)C_2H_4OC(O)OCH=CH_2$ (MeFOSEA) or $C_8F_{17}C_2H_4OC(O)OCH=CH_2$ (FOEA), require the polymer to be taken above its melt point and then cooled down to room temperature to form a highly repellent surface (i.e., a surface exhibiting a high receding contact angle to water and n-hexadecane).

Comparative Examples C1–C7

In Comparative Examples C1–C7, various known fluorochemical acrylate polymers outside the scope of this invention were evaluated for advancing and receding contact angles vs. water and n-hexadecane, using the same procedure as described in Examples 1–5.

In Comparative Example C1, Polymer 6, the simplest secondary alcohol-based fluorochemical acrylate polymer (i.e., where $R_f$ and $R_f'$ are both $CF_3$—) was evaluated. In Comparative Example C2, Polymer 7, a fluorochemical acrylate polymer having similar molecular architecture to Polymer 4, made by homopolymerizing $CH_2=CHC(O)OC_2H_4OCF=C(CF(CF_3)_2)_2$, was evaluated. Polymers 6 and 7 were both cured at ambient temperature (25° C.).

In Comparative Example C3, the fluorochemical acrylate polymer (Polymer 8) was similar to the polymers of this invention except that $R_f'$ was a straight chain perfluorohexyl group (i.e., not the required branched chain). Polymer 8 was cured at 150° C. before contact angle measurements were taken.

In Comparative Examples C4 and C5, Polymers 9 and 10, two crystalline fluorochemical acrylate homopolymers containing pendant $C_8F_{17}$— groups, were cured at 150° C. prior to contact angle measurements.

In Comparative Examples C6 and C7, Polymers 11 and 12, two relatively non-crystalline fluorochemical acrylate polymers containing $C_8F_{17}$— groups (made non-crystalline) by copolymerizing with n-butyl acrylate or by attaching butyl pendant groups to the perfluorosulfonamido sites, respectively), were cured at 150° C. prior to contact angle measurements. In this case, only water contact angle measurements were taken.

Results are presented in TABLE 3.

TABLE 3

| Ex. | Polymer | Melt Point (° C.) | Cure Temp. (° C.) | Water: ACA | Water: RCA | n-Hexadecane: ACA | n-Hexadecane: RCA |
|---|---|---|---|---|---|---|---|
| C1 | 6 | None | 25 | 101 | 81 | 66 | 56 |
| C2 | 7 | None | 25 | 106 | 84 | 63 | 49 |
| C3 | 8 | N/R* | 25 | 107 | 61 | 74 | 58 |
| C4 | 9 | 115 | 150 | 122 | 105 | 78 | 75 |
| C5 | 10 | 80 | 150 | 125 | 110 | 80 | 72 |
| C6 | 11 | None | 150 | 120 | 71 | N/R* | N/R* |
| C7 | 12 | None | 150 | 120 | 70 | N/R* | N/R* |

*N/R = not run

The data in TABLE 3 show that Polymers 6, 7 and 8, cured at room temperature similar to the polymers of TABLE 1, generally exhibited lower contact angles than did the polymers of this invention, indicating that not all amorphous fluorochemical acrylate polymers work equally well at providing a repellent surface. The structure of the perfluoroaliphatic groups $R_f$ and $R_f'$ and the molecular architecture associated with the perfluoroaliphatic groups must all fall within the range specified by this invention Polymers 9 and 10, crystalline MeFOSEA and FOEA homopolymers respectively, demonstrate very high advancing and receding water and hexadecane contact angles when heated to 150° C. and cooled to room temperature. However, they must be heated past their melt point temperatures of 115° C. and 80° C., respectively, to exhibit optimum repellency.

Polymers 11 and 12, fluorochemical acrylate polymers containing $C_8F_{17}$ groups, are no longer crystalline, resulting in substantially lower receding contact angles.

Examples 8–9 and Comparative Example C8

In Examples 8 and 9, Polymers 13 and 14 were compared in repellency to the fluoropolymer in 3M FLUORAD™ FC-732 Fluorochemical Coating (Comparative Example C8), a protective coating used in electrical applications (FC-732 is a 2% solution of a copolymer of 99/1 $C_7F_{15}CH_2OC(O)C(CH_3)=CH_2/CH_2=CHC(O)OH$ in $C_4F_9OCH_3$ available from 3M Company). To run these tests, each polymer solution was diluted with $C_4F_9OCH_3$ to 0.2% solids solution, coupons of 6061 T-6 bare aluminum (available from Metaspec Co., San Antonio, Tex., coupon size of 1 in (2.5 cm)×1 in (2.5 cm)×0.032 in (0.8 mm), polished, with hanging hole) were dipped into each diluted polymer test solution, each wafer was allowed to dry under ambient conditions, and advancing (Adv), static (Stat) and receding (Rec) contact angles were measured with n-hexadecane and deionized water.

Results are presented in TABLE 4.

TABLE 4

| Ex. | Polymer | n-hexadecane, °: | | Water, °: | |
|---|---|---|---|---|---|
| | | Adv | Rec | Adv | Rec |
| 8 | 13 | 67 | 49 | 110 | 42 |
| 9 | 14 | 65 | 40 | 114 | 30 |
| C8 | FC-732 | 71 | 46 | 109 | 57 |

The data in TABLE 4 show that the polymers of this invention performed similarity to the comparative fluorocopolymer containing longer perfluoroalkyl groups.

Examples 10–15 and Comparative Examples C9–C12

This series of examples and comparative examples was run to illustrate that Polymers 15 and 16, both copolymers of this invention, are useful as surfactants in lowering the surface tension of various liquid neat high surface energy organic materials (two different epoxies, plasticizer, polyol) and would thus be effective in promoting the wetting and spreading on low surface energy substrates of coatings formulations employing such organic materials.

In Comparative Example C9, the surface tensions of the organic materials were measured with no surfactant added.

In Examples 10–15, the surface tensions of Polymers 15 and 16, two polymers of this invention made by copolymerizing 25% fluorochemical monomer with 75% PLURONIC™ L-44 diacrylate monomer and containing pendant —O—CH($CF_2CF_3$)($CF(CF_3)_2$) and —O—CH($CF_2CF_2CF_3$)($CF(CF_3)_2$) groups, respectively, were measured in the same organic materials at levels of 0.1, 0.2 and 0.5 grams solids per 100 mL of material.

In Comparative Examples C10–C12, the surface tensions of Polymer 17, a comparative known surfactant copolymer of similar structural composition but containing pendant $C_4F9$— groups, were both measured in the same organic materials at levels of 0.1, 0.2 and 0.5 grams solids per 100 mL of solvent. The comparative copolymer was made by copolymerizing $C_4F_9SO_2N(CH_3)C_2H_4OC(O)CH=CH_2$ with PLURONIC™ L-44 acrylate monomer at a monomer weight ratio of 22/78, therefore Polymer 17 contained a slightly lower fluorochemical acrylate monomer percentage than did Polymers 15 and 16 (25/75).

Surface tension measurements in dynes/cm are presented in TABLE 5.

TABLE 5

| | | Grams | Surface Tension in: | | | | |
|---|---|---|---|---|---|---|---|
| Ex. | Polymer | Polymer | LG-56[1] | GPE[2] | DBP[3] | 6110[4] | 828[5] |
| C9 | None | 0 | 33 | 43 | 34 | 46 | 45 |
| 10 | 15 | 0.1 | 29 | 29 | N/R* | N/R* | 28 |
| 11 | 15 | 0.2 | 27 | 27 | N/R* | N/R* | 28 |
| 12 | 15 | 0.5 | 27 | 24 | N/R* | N/R* | 25 |
| 13 | 16 | 0.1 | 29 | 25 | 24 | 25 | 22 |
| 14 | 16 | 0.2 | 26 | 24 | 22 | 24 | 21 |
| 15 | 16 | 0.5 | 26 | 22 | 22 | 24 | 20 |
| C10 | 17 | 0.1 | 30 | 35 | 33 | 38 | 33 |
| C11 | 17 | 0.2 | 28 | 32 | 32 | 36 | 29 |
| C12 | 17 | 0.5 | 23 | 31 | 31 | 23 | 17 |

*N/R =not run
[1]ARCO ™ LG-56 polyol, available from ARCO, Los Angeles, CA.
[2]Glycidyl phenyl ether, available from Sigma-Aldrich Chemical Co.
[3]Dibutyl phthalate, available from Sigma-Aldrich Chemical Co.
[4]UVR ™ 6110 cycloaliphatic epoxy resin, available from CHEMCENTRAL Corp., Chicago, IL.
[5]EPON ™ 828-RS bisphenol A epoxy resin, available from Shell Chemical Co., Houston, TX.

The data in TABLE 5 show that the fluorochemical acrylate polymers of this invention generally had superior surface tension reducing properties to the polymer containing non-degradable $C_4F_9$— groups.

Examples 16–18 and Example 5

Using the general procedure described for Examples 1–5, advancing and receding angle vs. water and n-hexadecane were measured for Polymers 19–21, copolymers of $CH_2=CHC(O)—O—CH(CF_2CF(CF_3)_2)_2$ fluorochemical acrylate monomer and vinylidene chloride having monomer ratios varying from 80/20 to 95/5.

Results are presented in TABLE 6, along with contact angle measurements previously presented for $CH_2=CHC(O)—O—CH(CF_2CF(CF_3)_2)_2$ homopolymer (Polymer 5) as Example 5.

TABLE 6

| | | | Water: | | n-Hexadecane: | |
|---|---|---|---|---|---|---|
| Example | Polymer | % VCl$_2$ | ACA | RCA | ACA | RCA |
| 16 | 19 | 20 | 107 | 79 | 67 | 44 |
| 17 | 20 | 10 | 108 | 81 | 68 | 44 |
| 18 | 21 | 5 | 108 | 91 | 69 | 59 |
| 5 | 5 | 0 | 118 | 103 | 70 | 63 |

The data in TABLE 6 show that the amount of VCl$_2$ incorporated in the copolymer generally has little effect on advancing contact angles. However, the receding contact angles do decrease fairly linearly when the ratio of VCl$_2$ in the copolymer is increased. Thus, optimum overall repellency is realized employing a fluorochemical acrylate homopolymer.

Various modifications and alterations of this invention will become apparent to those skilled in the art without departing from the scope and spirit of this invention.

We claim:

1. A compound comprising at least two units of the formula

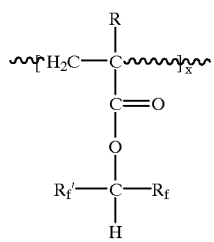

(I)

wherein ∼∼∼ represents a bond in a polymerizable or a polymer chain;

$R_f$ is a straight chain or branched perfluoroalkyl group with five or less carbon atoms;

$R_f'$ is a branched perfluoroalkyl group with three to five carbon atoms;

R is hydrogen, methyl, fluoro or chloro; and x is at least 2.

2. The compound of claim 1, wherein the compound is an oligomer containing from two to ten units of formula I.

3. The compound of claim 1, wherein the compound is a polymer containing greater than ten units of formula I.

4. The compound of claim 1, wherein the compound is a polymer containing from ten to fifty units of formula I.

5. The compound of claim 1, wherein $R_f$ is $CF_3$—, $CF_3CF_2$—, $CF_3CF_2CF_2$—, $(CF_3)_2CF$—, or $(CF_3)_2CFCF_2$—.

6. The compound of claim 5, wherein $R_f$ is $CF_3CF_2$— or $CF_3CF_2CF_2$—.

7. The compound of claim 1, wherein $R_f'$ is —$CF(CF_3)_2$ or —$CF_2CF(CF_3)_2$.

8. The compound of claim 7, wherein $R_f'$ is —$CF(CF_3)_2$.

9. The compound of claim 1, wherein said compound is a polymer having a glass transition temperature from about 0° C. to 60° C.

10. The compound of claim 1, wherein said compound is a homopolymer.

11. The compound of claim 1, wherein said compound is a copolymer.

12. The compound of claim 11, wherein said copolymer comprises comonomers chosen from the group consisting of: alkyl acrylate esters, vinyl acetate, vinylidene chloride, styrene, alkyl vinyl ethers, alkyl methacrylate esters, acrylic acid, methacrylic acid, acrylamide, methacrylamide, acrylonitrile, methacrylonitrile, polyoxyalkylene acrylate esters, and N-vinylpyrrolidone.

13. The compound of claim 12, wherein said comonomer is an alkyl acrylate ester.

14. A composition comprising at least one unit of the formula

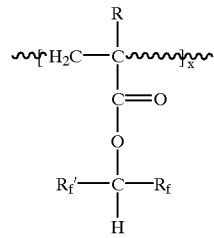

(I)

wherein, ∼∼∼ represents a bond in a polymerizable or a polymer chain, $R_f$ is a straight chain or branched perfluoroalkyl group with five or less carbon atoms, $R_f'$ is a branched perfluoroalkyl group with three to five carbon atoms, R is hydrogen, methyl, fluoro or chloro, and x is at least 1; wherein said composition is an aqueous solution or aqueous dispersion.

15. The composition of claim 14, wherein said composition is an aqueous dispersion.

16. The composition of claim 15, wherein said aqueous dispersion comprises from about 5 to 50 wt-% of said compound.

17. The composition of claim 16, wherein said aqueous dispersion comprises from about 0.5 to 15 wt-% of a dispersing and/or emulsifying agent.

18. A method of treating a substrate to render it oil- and/or water-repellent comprising the step of treating the substrate with a composition according to claim 14.

19. The method of claim 18, wherein said treatment of said substrate is accomplished by immersion, flooding, spraying, padding, foaming, kiss rolling, metering, or painting.

20. A method of coating an electrical device comprising applying a composition according to claim 14.

21. A method of coating optical fibers comprising applying a composition according to claim 14.

22. An article comprising a substrate treated with a composition according to claim 14.

23. The article of claim 22, wherein said substrate is a fibrous, or a hard surface substrate.

24. The article of claim 22, wherein said substrate is an optical fiber.

25. The article of claim 22, wherein said substrate is an electrical device.

26. A method of reducing the surface tension of a liquid comprising adding a compound according to claim 1 to said liquid.

27. The method of claim 26, wherein said compound is a copolymer.

28. The method of claim 27, wherein said copolymer comprises a polyoxyalkylene oxide acrylate ester.

* * * * *